US006958035B2

(12) United States Patent
Friedman et al.

(10) Patent No.: US 6,958,035 B2
(45) Date of Patent: Oct. 25, 2005

(54) MEDICAL DEVICE SHEATH APPARATUS AND METHOD OF MAKING AND USING SAME

(75) Inventors: Marc David Friedman, Needham, MA (US); Shawn Timothy Moynihan, Lowell, MA (US); Anthony Mark Smith, Medway, MA (US)

(73) Assignee: Dusa Pharmaceuticals, Inc, Wilmington, MA (US)

( * ) Notice: Subject to any disclaimer, the term of this patent is extended or adjusted under 35 U.S.C. 154(b) by 0 days.

(21) Appl. No.: 10/331,561

(22) Filed: Dec. 30, 2002

(65) Prior Publication Data

US 2004/0073088 A1 Apr. 15, 2004

Related U.S. Application Data

(60) Provisional application No. 60/418,664, filed on Oct. 15, 2002.

(51) Int. Cl.[7] .................................................. A61B 1/00
(52) U.S. Cl. ........................ 600/121; 600/114; 600/105
(58) Field of Search .......................... 600/121, 123–125, 600/114–116, 105; 604/27, 30, 43, 506

(56) References Cited

U.S. PATENT DOCUMENTS

| 5,105,800 A | | 4/1992 | Takahashi et al. |
| 5,855,549 A | * | 1/1999 | Newman ..................... 600/135 |
| 5,868,662 A | * | 2/1999 | Borodulin et al. .......... 600/105 |
| 6,293,909 B1 | | 9/2001 | Chu et al. |
| 6,741,884 B1 | * | 5/2004 | Freeman et al. ............ 600/473 |

* cited by examiner

*Primary Examiner*—Beverly M. Flanagan
(74) *Attorney, Agent, or Firm*—Reed Smith LLP

(57) ABSTRACT

A medical device sheath apparatus including: a fitting being suitable for receiving the medical device in a self sealing manner; a first sheath for receiving the medical device as it passes through the fitting; a second sheath surrounding the first sheath; a dilator defining a treatment area, coupled to at least the second sheath, and being suitable for dilating a bodily cavity and passing therapeutic or diagnostic energy in such forms as electromagnetic radiation or acoustic energy there through; and, a window operatively positioned with respect to the first sheath so as to enable viewing of an area substantially adjacent the second sheath upon insertion of the medical device into the apparatus.

27 Claims, 13 Drawing Sheets

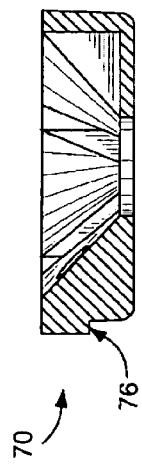
FIG. 4A
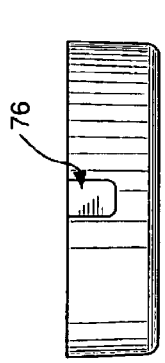
FIG. 4B
FIG. 4C
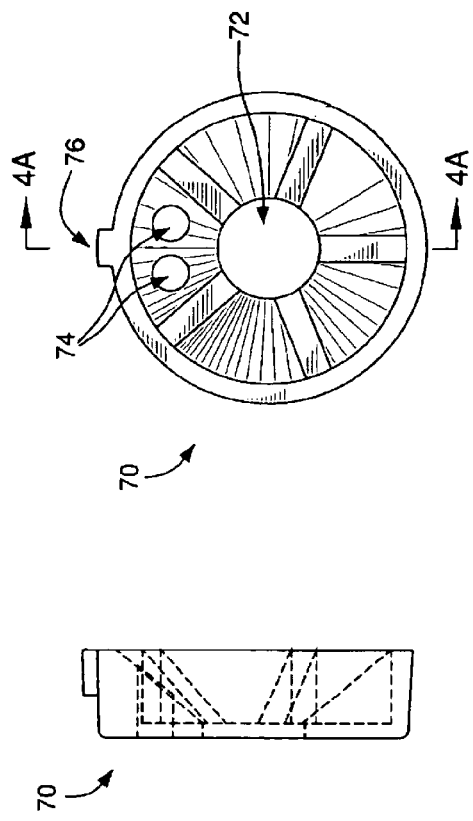
FIG. 4D
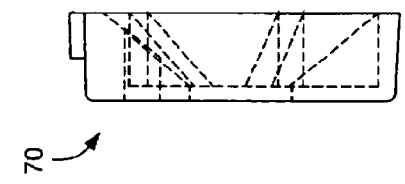
FIG. 4E
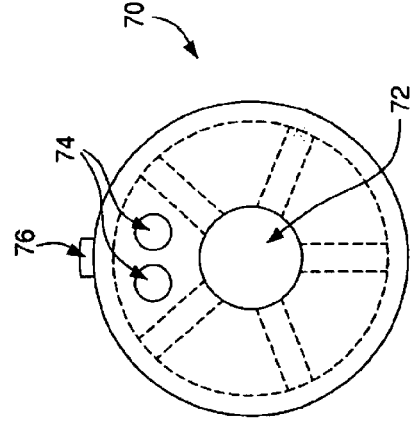

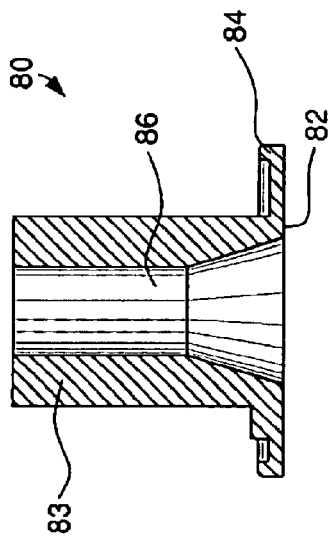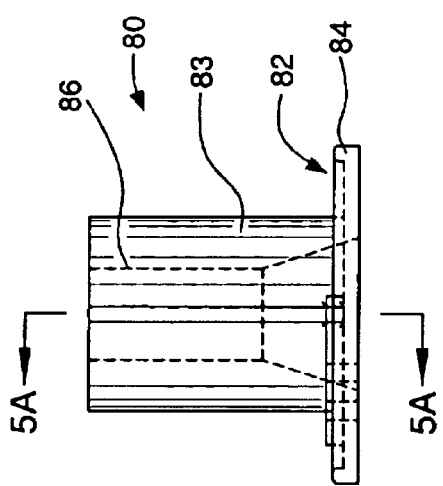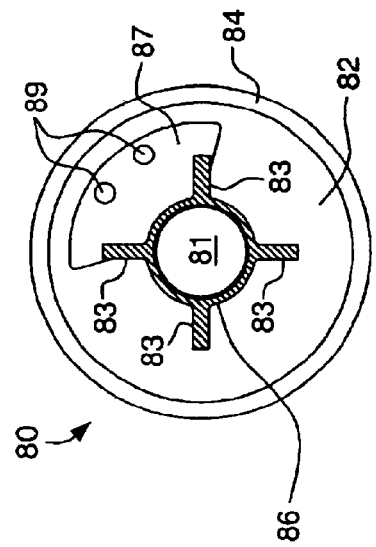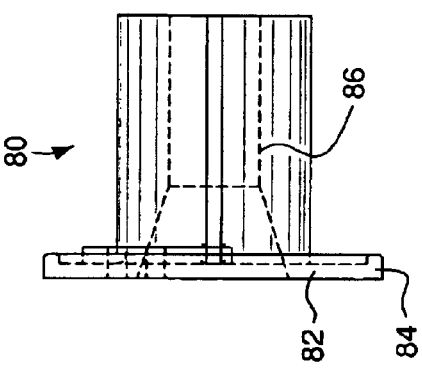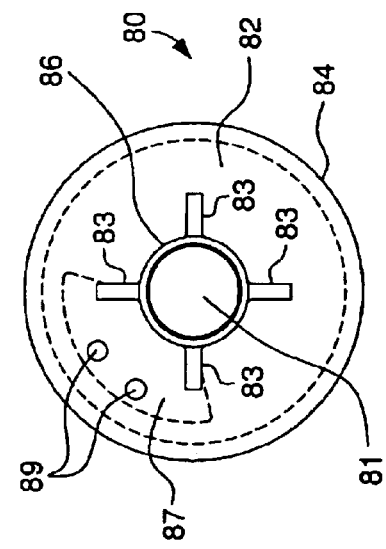

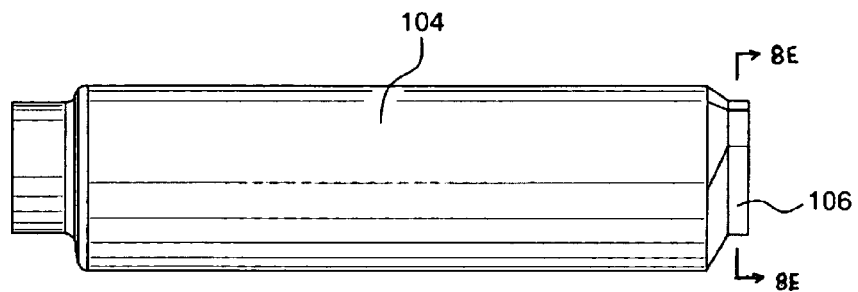
FIG. 8C
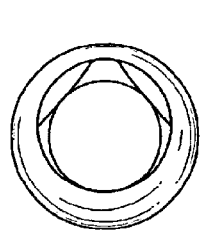 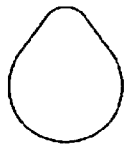 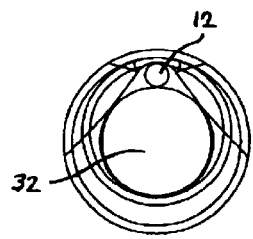
FIG. 8D  FIG. 8E  FIG. 8F

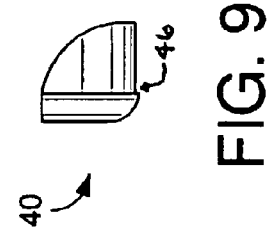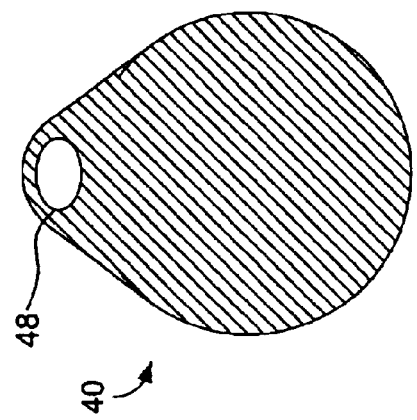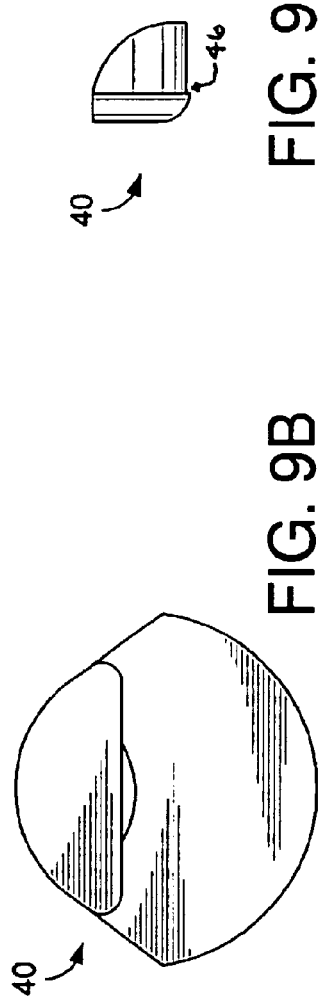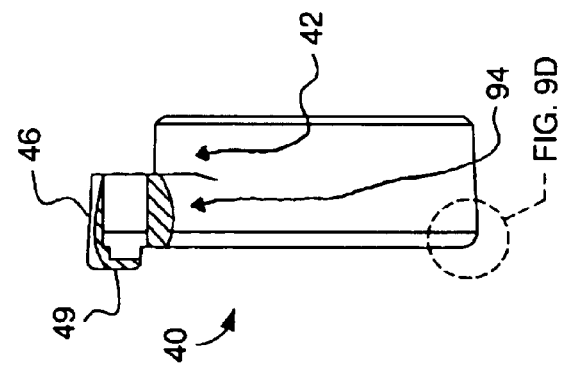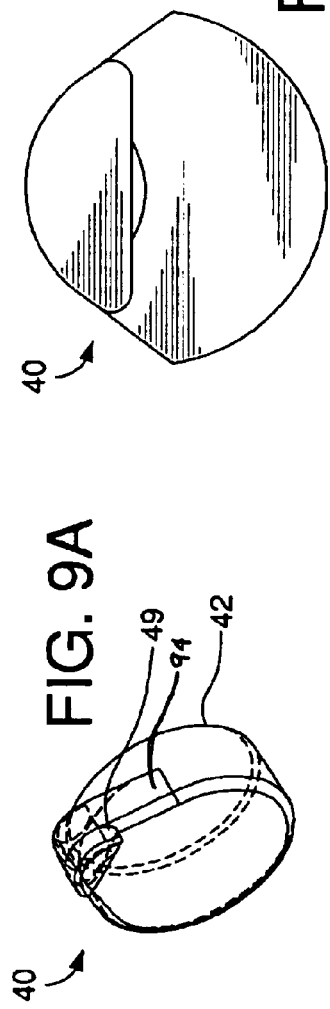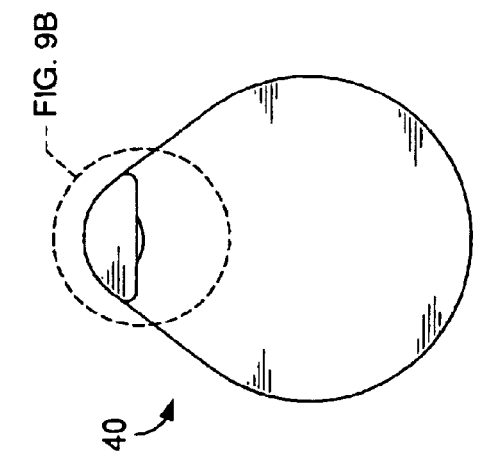

MEDICAL DEVICE SHEATH APPARATUS AND METHOD OF MAKING AND USING SAME

RELATED APPLICATION

This application claims priority of U.S. patent application Ser. No. 60/418,664, entitled MEDICAL DEVICE SHEATH APPARATUS AND METHOD OF MAKING AND USING SAME, filed Oct. 15, 2002, the entire disclosure of which is hereby incorporated by reference as if being set forth in its entirety herein.

FIELD OF THE INVENTION

The present invention relates generally to systems and methods for treating medical conditions, and more particularly to systems and methods for treating medical conditions associated with a body cavity or lumen.

BACKGROUND OF THE INVENTION

Endoscopes are generally used to examine various biological cavities, such as those in the alimentary canal or the bladder. Such may be biological cavities of a human or otherwise. A physician typically has a limited view of the interior of the cavity in which the distal end of the endoscope is located, due to the fact that tube like organs, such as the esophagus, intestine, and bladder, may be relatively soft and pliable such that the organ collapses about the endoscope. In order to have a better view of the cavity, air or liquid (such as water) may be traditionally forced into the cavity causing the cavity to temporarily expand.

Devices have generally been developed to distend tube-like organs with hardened or scarred tissue. One such device used by physicians is the balloon catheter. In the cardiovascular system, balloon catheters are used to open blocked or significantly narrowed arteries. In the gastrointestinal system, a modified balloon catheter, or balloon dilator, may be used to exert a radial force on the surrounding walls of tube-like organs, for the purpose of dilating strictures. Balloon dilators are commonly used in the gastrointestinal tract for strictures of the esophagus, pylorus, duodenum, sphincter of odi, biliary tree and colon.

Balloon catheters and dilators have also been used for expansion without the exertion of large radial forces. These balloon dilators are instead used to hold an organ open for an extended period of time, usually for a treatment of some kind. This treatment may include delivering medicaments to a specific site within the cardiovascular system, or the activation of a photosensitizing agent in a variety of organs, for example.

Devices have also been proposed to expand non-tubular organs in order to create a uniform surface for the activation of a photosensitizing agent. Such organs include the uterus and the bladder, for example.

Regardless, such distending devices may conventionally be positioned with respect to a target tissue with the aid of guidewires, or specialized introducers, being passed through the lumen of an endoscope, or by being passed "blindly" through connecting body lumens. However, there is typically no direct viewing of the positioning procedure or the target tissue. Therefore, difficulties exist in remotely and effectively treating a disease or ailment. Further, using guidewires typically requires, multiple insertions into the cavity to perform a treatment. Generally, the more insertions required, the greater the chance for damage to surrounding tissue. For example, in a typical guidewire related gastrointestinal PDT procedure, a physician typically first inserts an endoscope to determine the treatment site. Once the site is located, a guidewire is typically inserted into the instrument channel of the endoscope. The endoscope is then withdrawn and the guidewire is left behind at the treatment site. Next, a balloon dilator is typically inserted using the guidewire as a central axis. To view the site, the endoscope is then reinserted alongside the dilator. When the procedure is complete, all devices are removed from the site.

In situations where devices are passed either through an endoscope or are passed "blindly", there is a risk that the device may not be properly positioned at the target tissue, or more significantly, pass into unintended tissue and/or lumens causing harm to the patient. It is generally desirable to mitigate this risk. Further, it is generally desirable to minimize the number of insertions that must be performed to treat an area of interest.

SUMMARY OF THE INVENTION

A medical device sheath apparatus including: a fitting being suitable for receiving the medical device in a self sealing manner; a first sheath for receiving the medical device as it passes through the fitting; a second sheath surrounding the first sheath; a dilator defining a treatment area, coupled to at least the second sheath, and being suitable for dilating a bodily cavity and passing therapeutic or diagnostic energy in such forms as electromagnetic radiation or acoustic energy there through; and, a window operatively positioned with respect to the first sheath so as to enable viewing of an area substantially adjacent the second sheath upon insertion of the medical device into the apparatus.

A method for irradiating at least a portion of a bodily cavity including: providing a sheath apparatus including: a fitting being suitable for receiving the medical device in a self sealing manner; a first sheath for receiving the medical device as it passes through the fitting; a second sheath surrounding the first sheath; a dilator defining a treatment area, coupled to at least the second sheath, and being suitable for dilating a bodily cavity and passing therapeutic or diagnostic energy in such forms as electromagnetic radiation or acoustic energy there through; and, a window operatively positioned with respect to the first sheath so as to enable viewing of an area substantially adjacent to the second sheath upon insertion of the medical device into the apparatus; inserting at least a portion of the medical device into the apparatus; positioning the medical device containing apparatus in the bodily cavity using direct viewing through the window and the medical device; and, irradiating the portion of the bodily cavity through the apparatus using the medical device.

A method for making a medical device sheath apparatus including: coupling a first sheath to a fitting being suitable for receiving the medical device in a self sealing manner; coupling a second sheath to the fitting so as to surround the first sheath; coupling a dilator defining a treatment area and being suitable for dilating a bodily cavity and passing therapeutic or diagnostic energy in such forms as electromagnetic radiation or acoustic energy there through to the second sheath; and, coupling the first sheath to a window operatively positioned with respect to the first sheath so as to enable viewing of an area substantially adjacent the second sheath upon insertion of the medical device into the apparatus.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts, and,:

FIGS. 4A–4E illustrate various views of a seal retainer suitable for use with the fitting of FIG. 3;

FIGS. 5A–5E illustrate various views of a seal suitable for use with the fitting of FIG. 3;

FIGS. 8A–8F illustrate various views of an outer sheath suitable for use with the sheath lumens of FIGS. 7A–7D;

FIGS. 9A–9F illustrate various views of a distal window suitable for use with the apparatus of FIG. 1;

DETAILED DESCRIPTION OF THE PREFERRED EMBODIMENTS

Figure 1:
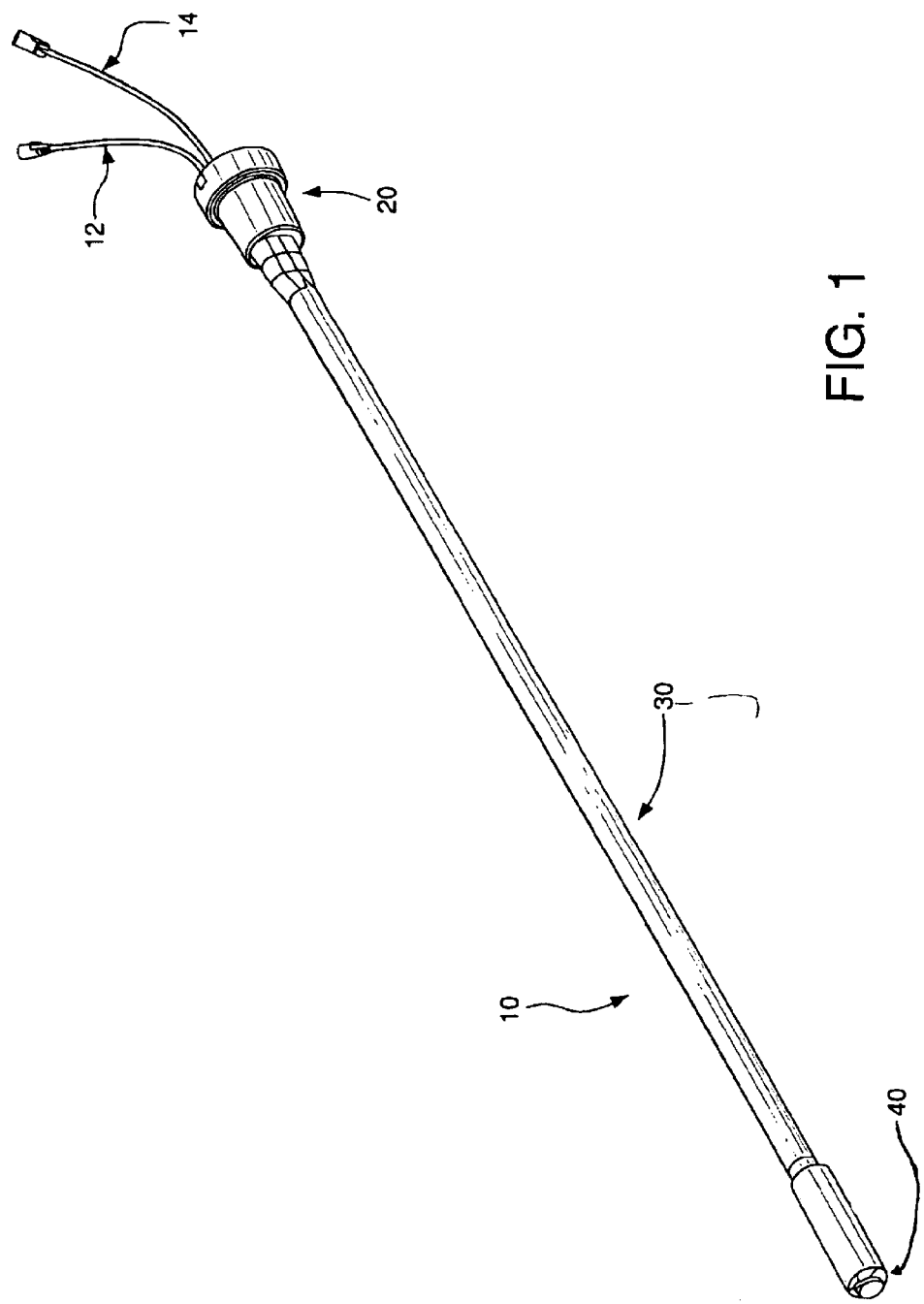
FIG. 1 illustrates an isometric view of an apparatus according to an aspect of the present invention.

It is to be understood that the figures and descriptions of the present invention have been simplified to illustrate elements that are relevant for a clear understanding of the present invention, while eliminating, for purposes of clarity, many other elements found in endoscopic systems and radiating treatment methods. Those of ordinary skill in the art will recognize that other elements are desirable and/or required in order to implement the present invention. However, because such elements are well known in the art, and because they do not facilitate a better understanding of the present invention, a discussion of such elements is not provided herein. The disclosure herein is directed to all such variations and modifications to such systems and methods known to those skilled in the art.

According to an aspect of the present invention, a sheath like apparatus may be provided and used that may be advantageously compatible with existing endoscopic equipment, and be used to expand, directly view and irradiate target tissue within a body cavity or lumen. It should be understood that while endoscope sheaths have generally been developed in order to prevent pathogen transfer from a cavity in which the scope is placed to the instrument itself, and in turn from person to person, these devices typically provide no other significant therapeutic benefits or advantages.

According to an aspect of the present invention, there is provided a sheath-like device which may be used in conjunction with, or otherwise associated with such as by substantially encasing, an endoscope and introduced into a body cavity or lumen. Such a device may allow the cavity or lumen, or portion thereof corresponding to a treatment area, to be formed or dilated to a desired shape, so as to be substantially spherical, cylindrical, ellipsoidal or ovoid, for example. According to an aspect of the present invention, such a device may provide means to inspect, diagnose and/or treat the cavity or lumen with electromagnetic radiation, such as light or acoustic energy such as ultrasound. Energy delivered in this manner may allow for more accurate diagnosis or treatment than may otherwise be conventionally possible. Provided energy may also effect treatment through direct physical effect on surrounding tissue, such as by cauterization or hypothermia, for example. Or, it may effect treatment by causing a chemical reaction, such as in conjunction with a photosensitizing agent or precursor present in target tissue, for example. According to an aspect of the present invention, enhanced visualization of the cavity or lumen being irradiated may be achieved.

According to an aspect of the present invention, there may be provided and used a sheath-like apparatus into which an endoscope may be inserted, so as to facilitate examination and therapy within a biological cavity using a single insertion of the apparatus. Near an end of the apparatus, a bladder or balloon portion positionable with the aid of an elongated sheath portion may be provided. The balloon portion may be inflated with a suitable fluid, such as a liquid or gas, to thereby cause it to swell and provide an outward force that may tend to dilate or deform a biological cavity into which it is inserted. Such dilation may be of a desirably and predictably smooth shape based upon characteristics of the balloon so as to enhance uniformity or irradiation or illumination provided therethrough. For example, the balloon may be substantially nondistensible. Alternatively, it may be desirable that the balloon portion be distensible or partially distensible based upon intended operational characteristics.

According to an aspect of the present invention, the apparatus may generally include a fitting which includes a seal housing, a seal which is dimensioned to receive an endoscope while creating a substantially air-tight seal about it, and a seal retainer. The apparatus may generally include a substantially transparent outer sheath including a non-distensible balloon; a substantially transparent inner sheath; a substantially transparent viewing window; a tube positioned between the inner and outer sheaths being suitable for delivering at least one fluid, such as air, to a distal end of the treatment apparatus, such as to terminate distal to the balloon and/or viewing window for the evacuation of matter that may accumulate distal to the balloon and/or window during therapy; and a second tube which terminates within the seal housing and is intended to transport a fluid or air for the purpose of inflating the balloon. The viewing window may have an antireflection coating on one or more surfaces.

The balloon may or may not have either a reflective, partially reflective or absorptive coating applied to one or more surfaces, or a portion thereof, to enhance and/or limit treatment to a specific target area of tissue within a cavity. The balloon may have an optical sensor or sensing fiber affixed to or embedded in it.

By inserting an endoscope into the apparatus, sufficient rigidity may be attained to allow the apparatus to be inserted into a biological cavity such as an esophagus. Once inside the esophagus, a physician may examine the inside of the esophagus by looking through the transparent viewing window, rinse the interior of the esophagus with water or saline that is introduced through the apparatus, introduce air, suction liquid, and properly position the apparatus for therapy. When properly positioned, air may be introduced into the balloon causing the balloon to inflate. The inflated balloon may substantially anchor the apparatus in the biological cavity allowing the endoscope to be withdrawn a distance equivalent to a treatment length. The treatment length may be determined through the endoscope by visual reference to markings within the apparatus or by visual reference to graduations on the endoscope itself, for example. An energy delivering device, such as a light emitting fiber, may then be inserted through an instrument channel in the endoscope, until it contacts the viewing window or a distal end of the apparatus, thereby exposing a portion of the energy delivering device to the cavity, such as a length of light emitting fiber suitable for treating a treatment area of tissue, i.e., a treatment length.

Referring now to FIG. 1, there is shown an isometric view of an apparatus 10 according to an aspect of the present invention. Apparatus 10 generally includes three functional areas: a proximal fitting 20, sheath lumens 30 and distal window 40. An air/water/suction line 12 and inflation/deflation line 14 are shown extending from the proximal fitting 20 of the apparatus 10.

Figure 2:
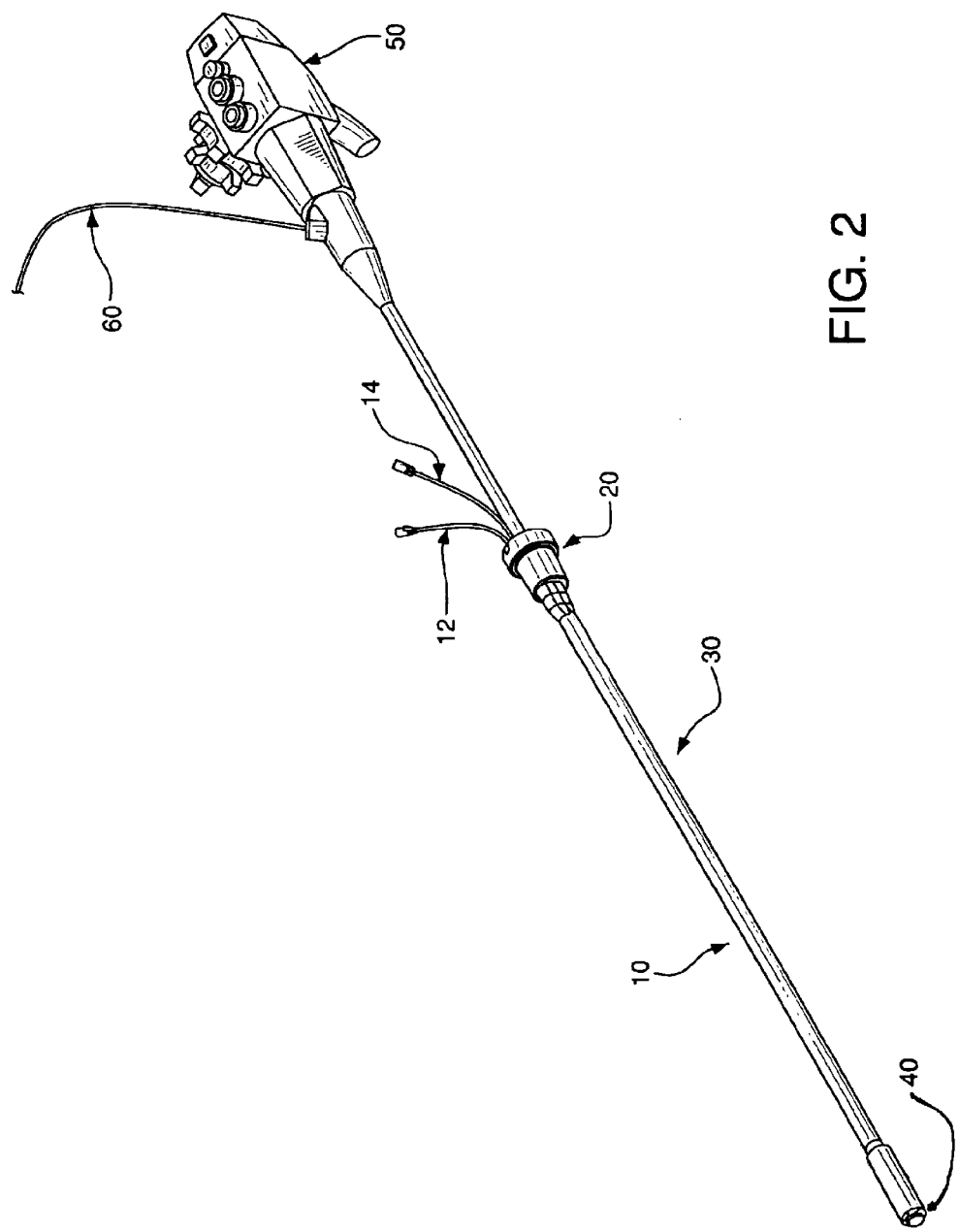
FIG. 2 illustrates an isometric view of the apparatus of FIG. 1 having a medical device partially inserted therein.

Referring now also to FIG. 2, there is shown an isometric view of the apparatus 10 of FIG. 1 having a medical device 50 partially inserted therein. Device 50 may generally take the form of an apparatus or instrument for visually examining the interior of a bodily canal or a hollow organ, such as the colon, bladder or stomach. Device 50 may take the form of an endoscope or gastroscope, for example. Device 50 may be referred to herein as an endoscope for purposes of non-limiting explanation only. Endoscope 50 passes through proximal fitting 20 and into an enclosed space formed by the sheath lumens 30. A radiation emitting device 60, such as a light emitting fiber, is shown extending through a biopsy or instrument channel of endoscope 50. Of course, any device being suitable for emitting radiation at wavelengths selected for therapeutic benefit of tissue and being inserted into device 50 may be used. Additionally, emitting device 60 may be connected to an activating source so as to couple emitted radiation into a treatment cavity and cause irradiation of surrounding tissue. For example, where device 60 takes the form of an optical fiber, a laser or other suitable light-generating device (not shown) optically coupled to the fiber may be used. Alternatively, device 60 may generate emitted radiation itself.

Terminal fittings of the air/water/suction line 12 and the inflation/deflation line 14 may be respectively connected to sources of air, water, or suction and pressure/vacuum respectively (not shown). Endoscope 50 may be used in conjunction with apparatus 10, such that proximal fitting 20 may provide a primary interface between apparatus 10 and endoscope 50. Proximal fitting 20 may further provide a grip by which to maneuver apparatus 10.

Figure 3:
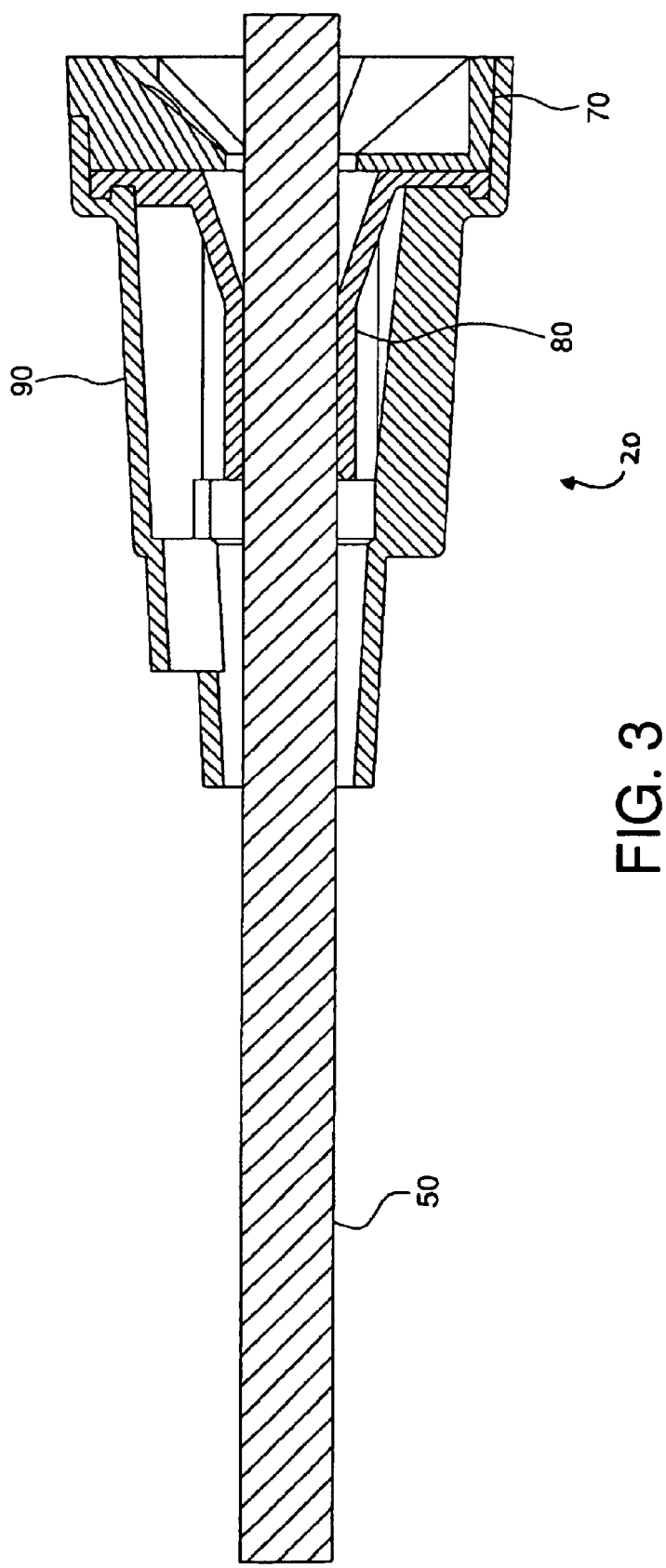
FIG. 3 illustrates a fitting suitable for use with the apparatus of FIG. 1.

Referring now also to FIG. 3, proximal fitting 20 generally includes a seal retainer 70, seal 80 and seal housing 90. Sealing may be largely accomplished using a suitable elastomeric material or, alternatively, a mechanically or pneumatically actuated seal. Seal retainer 70 and seal housing 90 may be acrylic in nature, but may be formed of any suitable, non-porous material that would allow for a good bonding surface for the other components as will be understood by one possessing an ordinary skill in the pertinent arts. Seal 80 may be formed of a parylene coated silicone, but may be largely formed out of any suitable elastomeric material that may have applied to it, a friction reducing coating. Seal retainer 70, seal 80 and housing 90 may be designed to take advantage of a repeatable manufacturing process, such as injection molding.

Referring now also to FIGS. 4A–4D, there are shown various views of a seal retainer suitable for use as seal retainer 70 of FIG. 3. Seal retainer 70 may generally take the form of a truncated cone having a small taper suitable for creating a locking fit with a mating portion of seal housing 90, as well to aid in ejection during a molding process, for example. A countersink like through hole or aperture 72 may be provided to guide a distal tip of endoscope 50 into place so as to pass through retainer 70 and into sheath portion 30 (FIGS. 1 and 2). Retainer 70 may also include two through holes or apertures 74 sized to fit a strain relief for inflation/deflation 12 and air/water suction 14 lines (FIGS. 1 and 2). Along an outer tapered surface of retainer 70 may be provided a key like feature 76 suitable for dictating positioning during assembly. This may serve to mitigate a risk of misalignment with mating holes in seal 80. Referring now also to FIGS. 5A–5D, there are shown various views of a seal suitable for use as seal 80 of FIG. 3. Seal 80 may be configured to provide multiple seals. Seal 80 may generally comprise a flat disk portion 82 and an o-ring-like gasket 84 that lies around a perimeter of the disk 82 and a tubular portion 86 extending longitudinally from disk 82. Seal 80 may further include a bore 81 through disk 82 and tubular portion 86. Tubular portion 86 may be relatively thin walled to accommodate bore 81. Disk 82 and o-ring 84 may be compressed between a distal face of seal retainer 70 and a step in a bore of seal housing 90 when assembled therewith.

Seal 80 may further include a plurality, such as four (4), fin like protrusions 83 extending outwardly from and along tubular portion 86 of seal 80. Of course, any suitable shape for portion 83 may be used though. These protrusions may serve to provide rigidity to tubular portion 86 to prevent roll back upon removal of endoscope 50. Second, when fully assembled in seal housing 90, the distal face of the fins may contact at least one protrusion within the housing 90 to prevent elongation and therefore narrowing of seal 80 when endoscope 50 is inserted through bore 81.

Seal 80 may further include apertures 89 passing through disk portion 82 and being suitable for passing air/water/suction line 12 and inflation/deflation line 14 therethrough. Apertures 89 may be undersized in comparison to tubes being passed through them. Further, disk 82 may include a relatively thicker portion 87 through which apertures 83 pass to provide a greater sealing surface along the length of the inserted lines 12, 14 as they pass through seal 80. Portion 87 of increased thickness may also be configured to act as a key, forcing alignment of apertures 89 of the seal 80 with apertures 74 through seal retainer 70 (FIG. 4A) as well as with apertures through seal housing 90 which correspond to lines 12, 14.

Seal 80 may provide a seal between seal retainer 70 and seal housing 90. Seal 80 may provide a seal about lines 12, 14 where they pass through apertures 89. Seal 80 may provide for a seal between an inner wall of tubular portion 86 and endoscope 50 when endoscope 50 is passed through bore 81. An inner diameter of tubular portion 86 may be relatively undersized, such that when endoscope 50 is passed therethrough, tubular portion 86 expands to allow endoscope passage.

Wall thickness and durometer of silicone composing seal 80 may be adjusted during manufacturing to obtain desired radial force operability. By adjusting the seal length and applying a parylene coating during manufacturing, the friction between the seal and the scope can be adjusted to allow for smooth insertion and removal of the endoscope into and from apparatus 10, for example. The desired friction may also be set so that movement of endoscope 50 relative to the sheath assembly 10 should not inadvertently occur during use, absent force being applied to endoscope 50 by a physician, for example. Tubular portion 86 may be tapered at one or both longitudinal ends to ease insertion and/or removal of endoscope 50, for example. As will be recognized by one possessing an ordinary skill in the pertinent arts, when all three seals are effected, apparatus 10 defines a substantially closed system that can be pressurized.

Referring now also to FIGS. 6A–6F, there are shown various views of a seal housing being suitable for use as seal housing 90 of FIG. 3. Seal housing 90 may serve primarily as a transition piece from seal 80 to sheath lumens 30 (FIG. 1). Housing 90 may generally take the form of a series of concentric cones forming a plurality of steps in an internal bore thereof, for example.

Housing 90 may include a portion 92 adapted to receive and position seal retainer 70. A first step that decreases the inner diameter of housing 90 may mate with flat disk portion 82 of seal 80, so as to cooperate as a sealing face. This first step may further include a small channel along its perimeter that mates with o-ring portion 84 of seal 80. A second portion 94 may include internally projecting fins 95 similar to fins 83 (FIG. 5A) to facilitate securing seal retainer 70 in a substantially centralized position within a bore of housing 90 and reduce seal elongation by retaining a proximal end of seal 80. Fins 95 may be spaced to facilitate alignment of seal 80. Substantially adjacent a longitudinal end of portion 94 substantially distal to portion 92, a small thin walled protrusion 93 that acts as a positive stop for fins 83 of seal 80, preventing elongation upon endoscope insertion, may be provided. Further, two apertures 97, 99 passing through this same end of portion 94 substantially distal from portion 92 may be provided. A larger of the two apertures 99 may be substantially centralized and sized to allow endoscope 50 passage. Aperture 99 may also pass through a tapered protrusion 98 that for a more proximal portion, substantially adjacent to section 94, may be teardrop shaped in cross section. An exterior surface of the tear dropped portion of protrusion 98 may serve as a bonding site for an outer sheath, as will be discussed. Protrusion 98 may then step down to a substantially circular cross-section, which may serve as a bonding site for an inner sheath, as will be discussed. Aperture 97 may be smaller, and adapted to pass through only the teardrop shaped portion of protrusion 98, exiting at or near the step down to the smaller, substantially circular cross-section. Aperture 97 may be used to provide access to a space between inner and outer sheaths, allowing for passage of the air/water/suction line 12 and inflation/deflation line 14. Aperture 97 may be positioned with reference to other keying features in the proximal fitting components to allow for a straight run, or substantially straight run, of the air/water/suction line 12 and/or inflation/deflation line 14.

Referring now also to FIGS. 7A–7D, there are shown various views of a sheath lumens suitable for use as sheath lumens 30 of FIG. 1. Sheath lumens 30 generally includes an inner sheath 32, air/water/suction line 12, inflation/deflation line 14, and an outer sheath/balloon 34. Inner sheath 32 and outer sheath/balloon 34 may be formed of Polyethylene Terephthalate (PET). Air/water/suction line 12 and inflation/deflation line 14 may be formed of Pebax 72D. Of course, either sheath 32, 34 or lines 12, 14 could be made out of any suitably flexible, thin walled plastic tubing or elastomeric material. According to an aspect of the present invention, an optically clear or radiation transmissive material may be utilized so as to pass treatment radiation therethrough and/or allow for direct visualization of an inflated biologic cavity. For example, non-compliant materials such as thermoplastics may make suitable choices.

Generally, inner sheath 32 may take the form of a thin walled (for example 0.001") tube that runs substantially the length of the sheath 30. A first end of inner sheath 32 may be tapered to fit over the tapered, circular cross section distal protrusion 98 of seal housing 90. An inner diameter of inner sheath 32 may be sized to allow passage of endoscope 50 therethrough. Inner sheath 32 may also serve to effectively limit an area in which optical fiber 60 (FIG. 2) used in treatment will be able to wander.

Generally, air/water/suction line 12 may be small in diameter (for example having a 0.072" outer diameter) and run substantially the length of sheath 30. Line 12 may terminate substantially at or near distal window 40. As set forth, line 12 may further pass through proximal fitting 20. Further, from the proximal fitting 20 a length of tubing may continue as a pigtail, terminating at a luer lock fitting, for example. To prevent movement of line 12, it may be banded to inner sheath 32. Accordingly, endoscope 50 may be effectively insulated from air/water/suction line 12 by inner sheath 32.

Figure 6A:
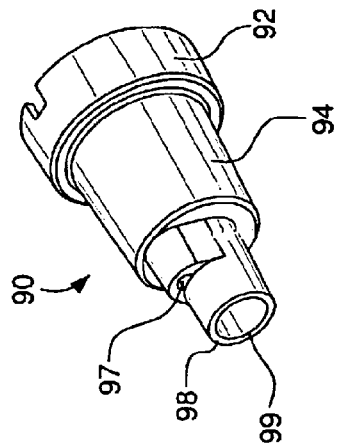
FIGS. 6A–6F illustrate various views of a seal housing being suitable for use with the fitting of FIG. 3.
Figure 6B:
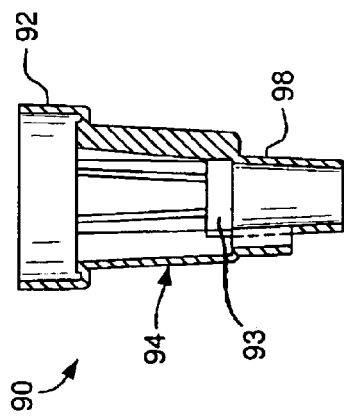
Figure 6C:
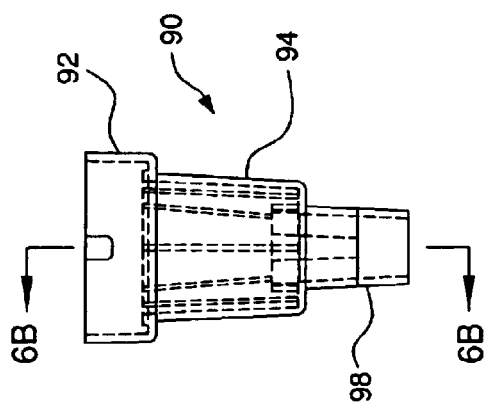
Figure 6F:
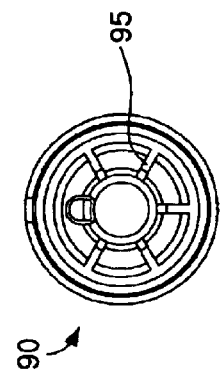
Figure 6E:
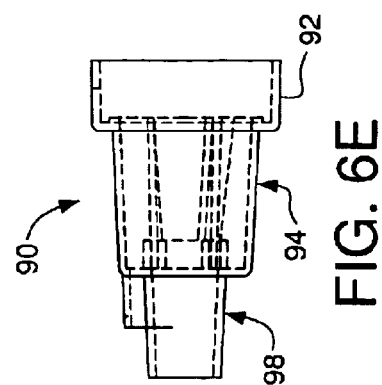
Figure 6D:
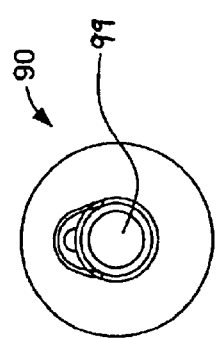
Figure 7A:
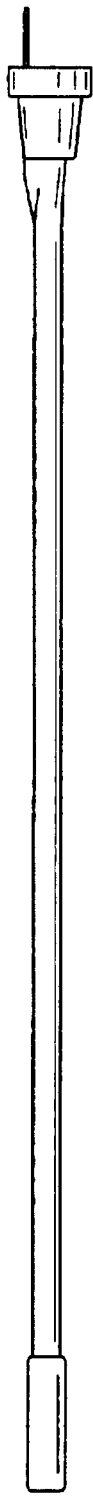
FIGS. 7A–7D illustrate various views of a sheath lumens suitable for use with the apparatus of FIG. 1.
Figure 7B:
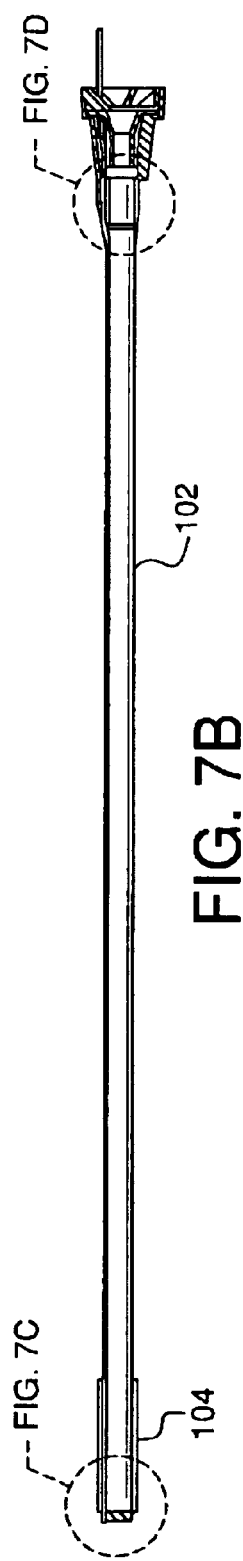
Figure 7D:
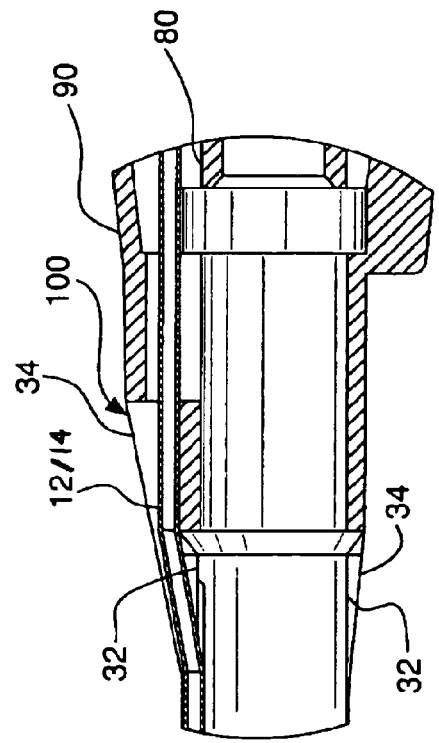
Figure 7C:
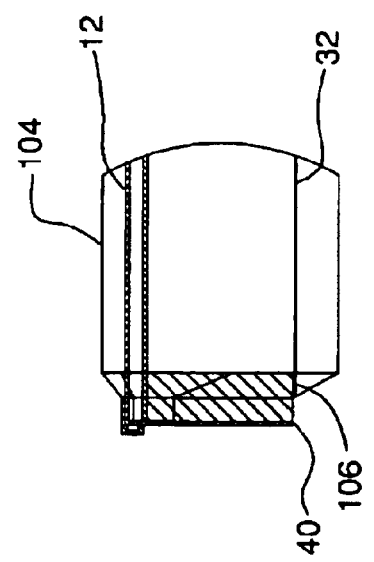
Figure 8A:
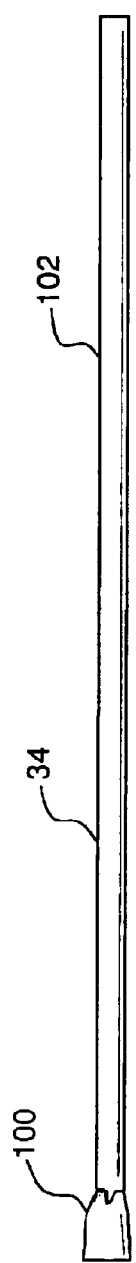
Figure 8B:
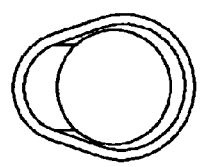

Generally, inflation/deflation line 14 may be small in diameter (for example having a 0.072" outer diameter) and terminate in a substantially free floating manner within seal housing 90 (FIG. 6A). As set forth, line 14 may further pass through proximal fitting 20. Further, from the proximal fitting 20 a length of tubing may continue as a pigtail, terminating at a luer lock fitting, for example. To prevent movement of line 14, it may also be banded to inner sheath 32. Accordingly, endoscope 50 may be effectively isolated from inflation/deflation line 14 by inner sheath 32.

Referring now also to 8A–8F in conjunction with 7A–7D in particular, there are shown various views of an outer sheath suitable for use as outer sheath/balloon 34 of FIGS. 7A–7D. According to an aspect of the present invention, outer sheath/balloon 34 may be seen to generally include a proximal taper 100, a cylindrical main lumen 102, a balloon 104 and a distal mating portion 106. The last two features can be a separate component from the other two, or integrally formed therewith. The outer sheath/balloon 34 may take the form of a thin walled (0.001") tube. A cross section of taper 100 may be generally tear drop in shape, designed to mate with the protrusion 98 of the same shape of seal housing 90. An elongated cylindrical main lumen 102 may be set off-axis from inner sheath 32 so as to allow for the passage of the air/water/suction line 12. A small cavity may be formed between inner sheath 32 and outer sheath 34 along the length. The shape of balloon portion 104 may at least partially depend on the type of biological cavity it is intended to be inflated in. In the illustrated, non-limiting instance it is shown as cylindrical, with an abrupt proximal and distal ending that may be suitable to fit within a patient's esophagus. The length and diameter of the balloon 104 cylinder can be manufactured in a variety of sizes depending on treatment requirements. Balloon 104 may also be coated on specific sections or in a pattern like manner to provide a specific treatment area, improve light efficiency to the treatment area, or improve uniformity, for example. Suitable coatings may be reflective, such as titanium oxide, gold, aluminum, silver or other metals in the case of light irradiation. Suitable coatings may be absorptive, such as carbon black in the case of light irradiation. Such coating may at least partially define treatment area within a biological cavity which balloon 104 is inserted, by facilitating unidirectional irradiation for example. Balloon 104 may be semipermeable, to allow an oxygenated fluid passage to tissue being treated. Distal mating portion 106 may be of a generally teardrop cross section that is designed to mate with distal window 40 (FIG. 1). This section 106 may be positioned so as to realign the axis of the outer sheath 34 to the inner sheath 32 and distal window 40 (FIG. 1). The balloon portion may be bonded to outer sheath main lumen 102.

Referring now also to FIGS. 9A–9F, there are shown various views of a distal window suitable for use as distal window 40 of FIG. 1. Generally, distal window 40 may take the form of a substantially planar, non-planar or lens shaped member, by way of non-limiting example only, that may be made of acrylic to provide a substantially optically clear, non-distorting window. Of course, any other material that provides these features and may be bonded to may be acceptable for use. Window 40 generally includes a tapered protrusion 42 with a circular cross section to provide a bonding site for inner sheath 32 (FIGS. 7A–7D). Window 40 may then step up to a tapered section 94 with a teardrop cross section suitable for providing a bonding site for outer sheath/balloon 34. A small ridge 46 may serve as a positive stop for outer sheath/balloon 34. Passing through the bonding site for the outer sheath/balloon 34 may be a small oval or ellipse shaped bore 48, which has a small step within it, and is hooded 49 on an end opposite to protrusion 42. Bore 48 may be designed to accept a distal end of the air/water/suction line 12 such that the internal step is positioned to act as a positive stop preventing over insertion. Hood 49 may serve to direct a stream of fluid passing through air/water/suction line 12 down across distal window 40. The deflecting surface of the hood may be angled so that the fluid passes over an outer surface of window 40. Viewing windows may be placed at other positions relative to balloon 104 as will be well understood by those possessing an ordinary skill in the pertinent art though. Further, viewing may be facilitated directly through balloon 104, for example, such that balloon 104 itself forms a viewing window.

Figure 10:
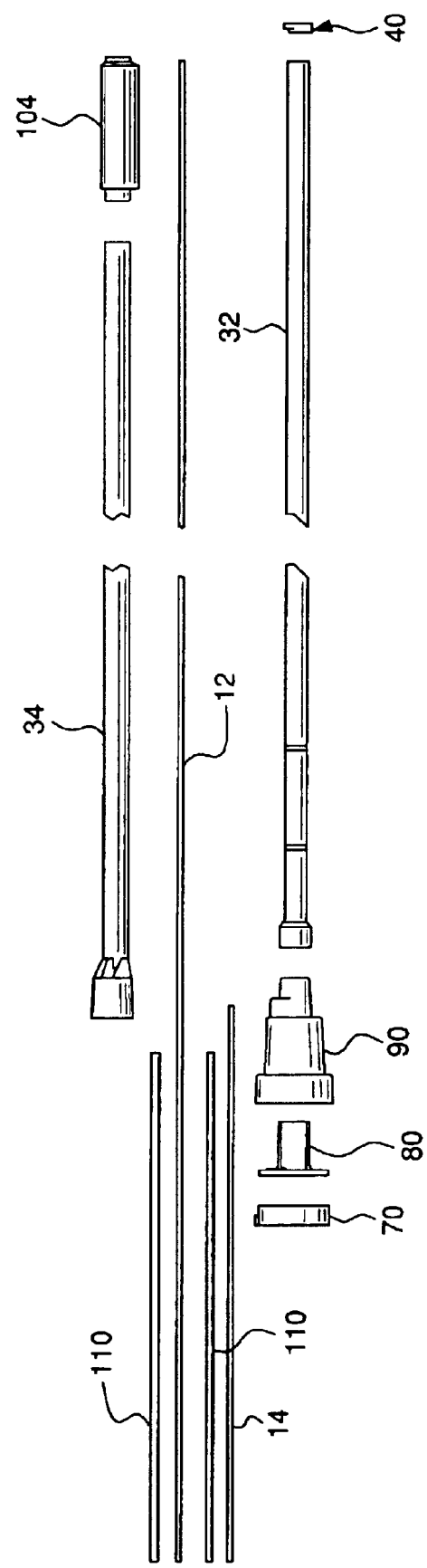
FIG. 10 illustrates an exploded view of the apparatus of FIG. 1.

Referring now also to FIG. 10, there is shown an exploded view of an embodiment of apparatus 10 of FIG. 1. Apparatus 10 of FIG. 10 may be assembled in the following manner. Inner sheath 32 may be adhered to seal housing 90. The air/water/suction line 12 may be fed through aperture 97 in seal housing 90 such that a length slightly longer than the distal end of inner sheath 32 is provided. The air/water/suction line 12 may then be banded to the inner sheath 32. An area of the inner sheath 32 corresponding to balloon 104 is preferably not banded. Outer sheath 34 may then be adhered to housing 90. Balloon 104 may then be slid onto the outer sheath 34 such that a distal end of balloon 104 is behind, or shorter than, a distal end of inner sheath 32. Air/water/suction line 12 may then be fed into and secured within aperture 48 of window 40, such as by adhering. Inner sheath 32 may then be adhered to the corresponding area of portion 42 of distal window 40, taking care to ensure that the air/water/suction line 12 remains substantially in-line. Balloon 104 may then be adhered up to the ridge 46 on window 40 and to the outer sheath 34. Seal 80 may then be inserted into seal housing 90 while feeding air/water/suction line 12 through one of the apertures 89, such as a left one, taking care to ensure full seating of seal 80. Inflation/deflation line 14 may then be fed through the other of the apertures 89 in the seal 80. The air/water/suction and inflation/deflation lines 12, 14 may then be fed through apertures 74 of seal retainer 70. Seal retainer 70 may then be fully seated within housing 90 such that the proximal faces thereof are substantially in plane. The air/water/suction and inflation/deflation lines 12, 14 may then be cut to provide pigtails of appropriate length, such as 25 cm. Strain reliefs 110 may then be slid onto and adhered to the ends of the air/water/suction and inflation/deflation lines 12, 14. Suitable strain reliefs may take the form of thin Pellethane tubes, for example. Female luer locks may then be secured to the free ends of the air/water/suction and inflation/deflation lines 12, 14, and attached to the strain reliefs.

In use, endoscope 50 may be inserted through the seal retainer 70, seal 80 and seal housing 90, and into the inner sheath 32 such that the distal end of the endoscope 50 becomes proximate to the distal end of the inner sheath 32 (i.e., adjacent to the viewing window 40). When endoscope 50 is fully inserted, sheaths 32, 34 may become less flexible in nature due to the more radially rigid endoscope 50 housed within them and is ready to be used in a biological cavity (e.g., an esophagus).

When the distal portion of endoscope 50 is proximate to the distal end of the inner sheath 32, endoscope 50 may be positioned to receive, and transmit, images of a cavity in which the sheath and endoscope are inserted; through the viewing window 40. If the viewing window becomes hazy or is covered by matter (which may be, for example, biological in nature), a physician can direct water or air through the air/water/suction line 12 to remove the matter from the viewing window 40. Similarly, if sufficiently small matter and/or fluid in nature should become adjacent to window 40, the matter may be removed by sucking it through the air/water/suction line 12.

By injecting a suitable material, such as a gas, air or liquid for example, between the inner and outer sheaths 32, 34 (by using inflation/deflation line 14 for example), balloon 104 will tend to inflate and deform a biologic cavity in which it is inserted. Similarly, if fluid pumped into apparatus 10 is withdrawn (for example, by sucking the fluid back out through inflation/deflation line 12), the space between inner and outer sheaths and between the inner sheath and endoscope scope will deflate.

Figure 11A:
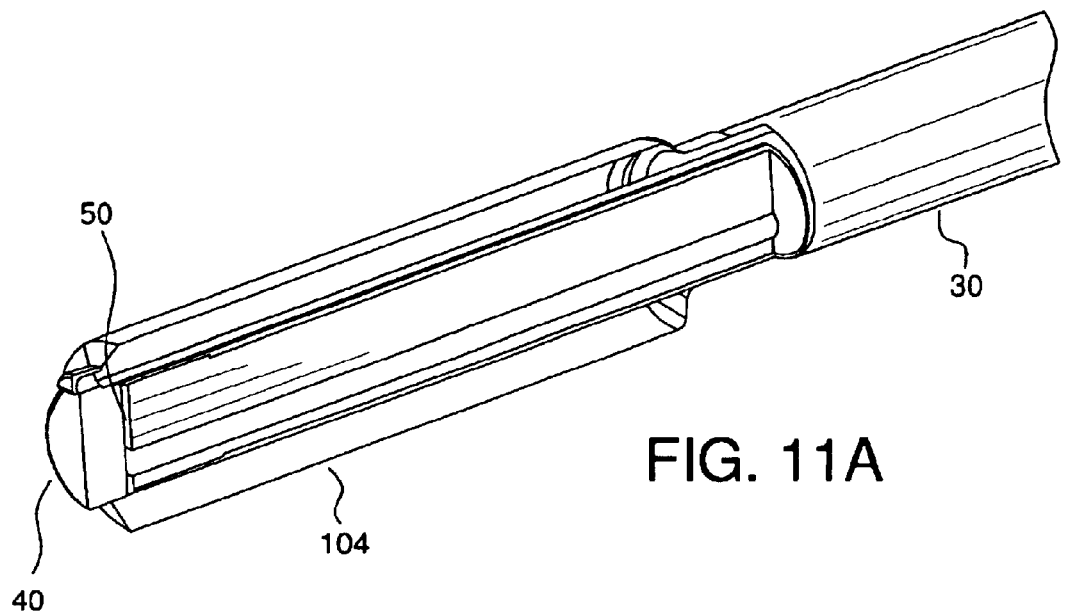
FIGS. 11A–11C illustrate cross-sectional views of the apparatus of FIG. 2, having an endoscope positioned at various positions therein for treatment.
Figure 11B:
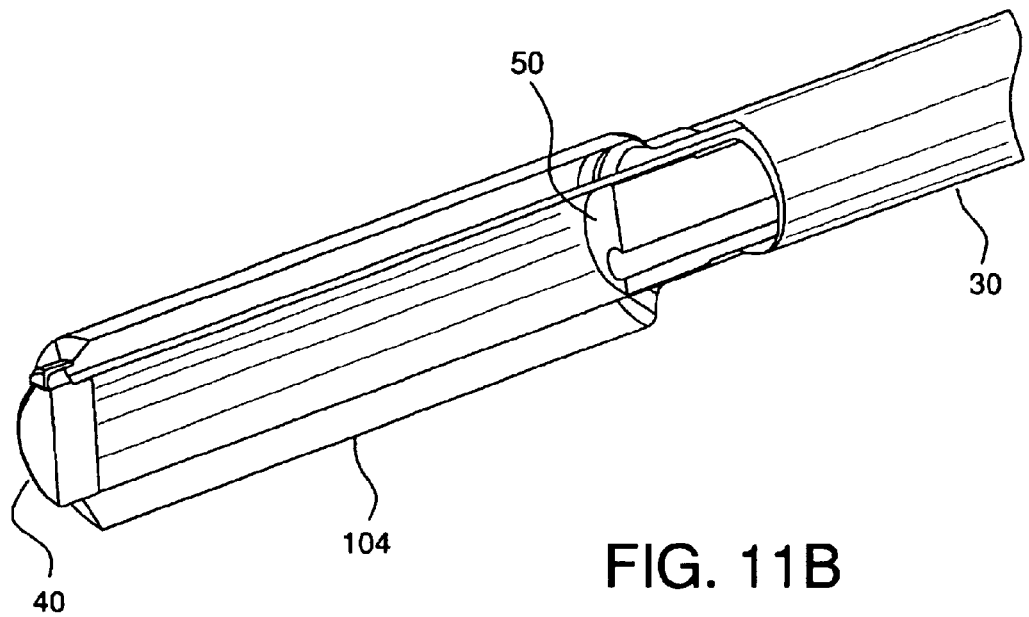

Referring now to FIGS. 11A and 11B, there are illustrated cross-sectional views showing the distal end of the endoscope 50 at a first position proximate the distal end of the inner sheath 32 wherein the balloon 104 is in a deflated state and adjacent a target region of a biologic cavity. When in this first position, the balloon 104 may be inflated (by pumping air, water, etc. through the inflation line 12 to expand the target region by making a uniform shape, for example). Simultaneously, the space between the inner and outer sheaths 32, 34, and/or between the inner sheath and the endoscope may be inflated.

The target region may be affected by a disease or ailment such as Barrett's Esophagus and may additionally contain a photosensitizing agent or precursor such as that described in U.S. Pat. Nos. 5,955,490, 5,422,093, 5,234,940, 5,211,938, 5,097,262 and in James C. Kennedy et al., *Photodynamic Therapy (PDT) and Photodiagnosis (PD) Using Endogenous Photosensitization Induced by 5-Aminolevulinic Acid (ALA): Mechanisms and Clinical Results*, 14 J. CLINICAL LASER MEDICINE & SURGERY 289–304 (1996), each of which is incorporated herein by reference in its entirety.

After the balloon 104 is inflated, the physician may pull on the endoscope 50 while holding the proximal fitting 20 thereby withdrawing the endoscope 50 relative to the viewing window 40; the endoscope being proximally withdrawn to a second position, thereby defining a treatment region between the distal end of the endoscope 50 and the proximal end of the viewing window 40 (FIG. 11B).

Figure 11C:
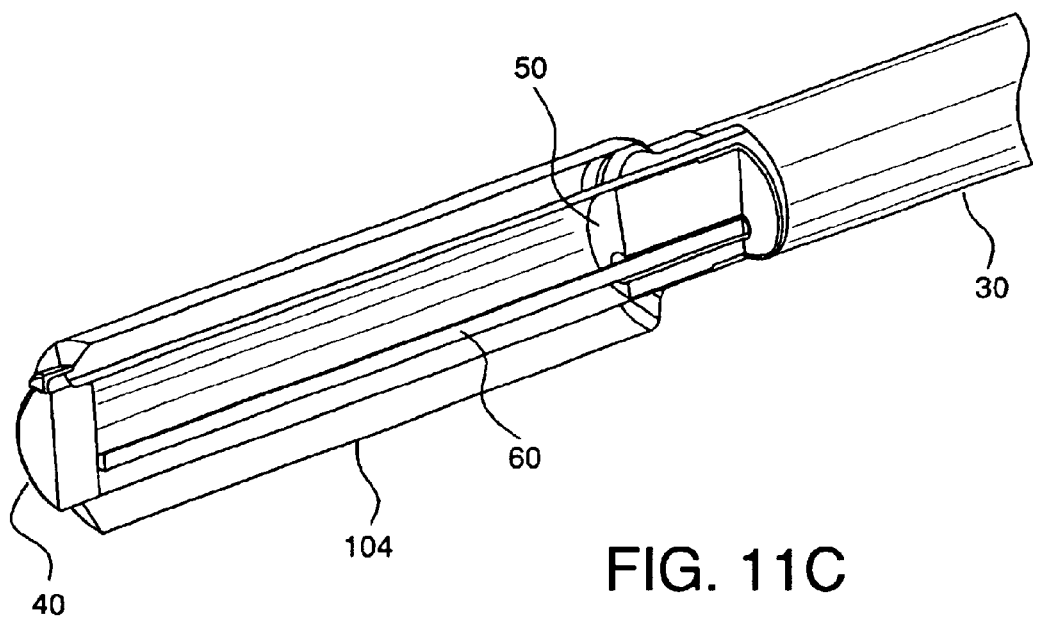

Referring now also to FIG. 11C, after the endoscope 50 is withdrawn, light emitting fiber 60 may be extended through the bores of apparatus 40, such that it projects into the treatment region between the distal end of the endoscope 50 and the proximal end of the viewing window 40. When the fiber 60 is extended, the physician may irradiate the target region with light. The light, which may take the form of laser emissions, passes through the inner sheath 32 and the balloon 104 of the outer sheath/balloon 34 and is absorbed by portions biologic cavity in which it is inserted, including the target region. The light delivered by the fiber may be in the infrared, visible, and/or ultraviolet regions of the spectrum, although if the intended treatment utilizes a photosensitizer, the wavelengths of light will be specific to those capable of activating said photosensitizer. The fiber that delivers the light may be configured in a variety of geometries including cylindrical, spherical and spot projection, with the preferred embodiment being cylindrical.

After the target region has been effectively treated, the combination of the endoscope 50, inner sheath 32, and outer sheath 34 may be removed in a manner similar to that by which the combination was inserted. Specifically, the light emitting fiber 60 may be withdrawn back into the endoscope 50, and the endoscope 50 is pushed back to the first position at which its distal end is proximate to the distal end of the inner sheath 32, while the balloon 104 remains inflated. Subsequently, the balloon 104 may be deflated. After deflating the balloon 104, the combination of the endoscope 50, inner sheath 32, and outer sheath 34 may be removed from the biologic cavity, such as an esophagus. Alternatively, apparatus 10 may be left in place to facilitate effecting other treatments or procedures, in which case endoscope 50 may be withdrawn, and if necessary or desirable, balloon 104 inflated to maintain its relative position in the cavity while endoscope 50 is being withdrawn.

According to an aspect of the present invention, seal 80 may take the form of a locking or passive seal.

According to an aspect of the present invention, air/water/suction line 12 could be split into an air/water line and a suction line. The air/water line would continue to use the hood feature on the distal window for displacing the spray of fluid. The suction line may be provided with a separate bore through the distal window 40 that was not hooded, to allow direct suction for example. An additional suction port could be positioned proximal to the balloon to remove fluid build up during treatment. According to an aspect of the present invention, air/water/suction line 12 could be removed altogether, which could allow for the removal of the outer sheath and the necessary bonding sites on the proximal fitting 20 and distal window 40. In such a case, balloon 104 may be adhered proximally and distally to the inner sheath 32. The inner sheath 32 may be allowed to communicate with the balloon 104.

According to an aspect of the present invention, air/water/suction line 12 could be removed altogether, which could allow for the removal of the inner sheath and the necessary bonding sites on the proximal fitting 20 and distal window 40. In such a case, balloon 104 may be adhered proximally and distally to the outer sheath. The outer sheath may be allowed to communicate with the balloon 104.

According to an aspect of the present invention, the inflation/deflation line could be removed and an air and suction feature inherent to endoscope 50 used to inflate and deflate the sheath respectively.

According to an aspect of the present invention, markings may be provided so as to be viewable using endoscope 50. According to an aspect of the present invention, reference points for determining a distance that the endoscope is withdrawn for treatment may take the form of markings at the distal end of the air/water/suction line 12 within the region of the balloon 104, inner sheath 32 or outer sheath 34, for example. This would allow the user to directly view how far back endoscope 50 is moved.

According to an aspect of the present invention, it may be desirable to at least partially inflate balloon 104 to improve viewing through window 40.

Although the aforementioned describes preferred embodiments of the invention, the invention is not so restricted. It will be apparent to those skilled in the art that various modifications and variations can be made to the disclosed preferred embodiments of the present invention without departing from the scope or spirit of the invention. For example, although the invention was described as being used in a esophagus, it could be used in any biological cavity sized to receive an endoscope (e.g., bladder, colon, etc.). In addition, although the invention was described as treating Barrett's Esophagus, it could be used to treat or diagnose other diseases or ailments such as colon or bladder cancer.

According to an aspect of the present invention, fiber 60 may be replaced by, or supplemented with, another medical treatment device or apparatus. By way of nonlimiting example, one or more ultrasound applicators could be sheathed by apparatus 10 so as to permit treatment, or the application of a procedure, to tissue via a cavity in which apparatus 10 has been inserted.

Accordingly, it should be understood that the apparatus and method described herein are illustrative only and are not limiting upon the scope of the invention, which is indicated by the following claims. Accordingly, alternatives which would be clear to one of ordinary skill in the art upon reading the teachings herein disclosed, are hereby within the scope of this invention.

What is claimed is:

1. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus;

wherein said fitting comprises: a seal housing: and, a seal secured by said housing and comprising a bore being suitable for receiving said medical device and sized to provide an air seal against an outside diameter of said medical device; and further comprising at least one additional bore being suitable for receiving at least one tube for inflating or deflating said dilator.

2. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus;

wherein said fitting comprises: a seal housing; and, a seal secured by said housing and comprising a bore being suitable for receiving said medical device and sized to provide an air seal against an outside diameter of said medical device; and wherein said seal is mechanically or pneumatically actuatable.

3. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus; and wherein said dilator further comprises at least one of a partially reflective coating and an absorptive coating.

4. The apparatus of claim 3, wherein said coating comprises at least one of gold, aluminum, silver, titanium oxide and carbon black.

5. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus;

wherein said fitting comprises: a seal housing, a seal secured by said housing and comprising a bore being suitable for receiving said medical device and sized to provide an air seal against an outside diameter of said medical device, and at least one retainer securing said seal to said housing; and wherein at least two of said housing, seal and retainer are keyed.

6. The apparatus of claim 5, wherein said keying comprises at least one notch.

7. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus:

wherein said fitting comprises: a seal housing, a seal secured by said housing and comprising a bore being suitable for receiving said medical device and sized to provide an air seal against an outside diameter of said medical device, and at least one retainer securing said seal to said housing; and wherein said seal comprises a plurality of fins suitable for mating with at least said housing or retainer.

8. A The apparatus of claim 7, wherein at least one of said housing and retainer comprise a plurality of grooves suitable for receiving said fins.

9. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus; and further comprising means for inflating at least said dilator.

10. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus;

wherein said fitting comprises: a seal housing, a seal secured by said housing and comprising a bore being suitable for receiving said medical device and sized to provide an air seal against an outside diameter of said medical device, and at least one retainer securing said seal to said housing; and wherein said retainer comprises a plurality of channels.

11. The apparatus of claim 10, wherein said housing comprises a plurality of projections positioned to mate with said channels when said retainer and housing are coupled to one another.

12. A medical device sheath apparatus comprising: a fitting being suitable for receiving said medical device in a self sealing manner; a first sheath for receiving said medical device as it passes through said fitting; a second sheath surrounding said first sheath; a dilator defining a treatment area, coupled to at least said second sheath, and being suitable for dilating a bodily cavity and passing therapeutic electromagnetic radiation there through; and, a window operatively positioned with respect to said first sheath so as to enable viewing of an area substantially adjacent said second sheath upon insertion of said medical device into said apparatus;

wherein said fitting comprises: a seal housing; and, a seal secured by said housing and comprising a bore being suitable for receiving said medical device and sized to provide an air seal against an outside diameter of said medical device; and wherein said seal comprises: a disc portion; an o-ring peripherally positioned with respect to said disk portion; and, a tubular portion extending from said disk portion; wherein said disk portion and tubular portion define at least one bore suitable for receiving said medical device there through.

13. The apparatus of claim 12, wherein said tubular portion comprises a plurality of radially outwardly extending protrusions.

14. The apparatus of claim 13, further comprising at least one aperture passing through said disk portion, wherein said disk portion is adapted to be compressed between said housing and retainer.

15. The apparatus of clam 14, wherein said housing defines an internal bore corresponding to said bore of said seal, and said housing bore comprises a plurality of internal steps.

16. The apparatus of claim 15, wherein said housing further comprises a first bonding location for said first sheath and a second bonding location for said second sheath.

17. The apparatus of claim 16, wherein said housing further comprises at least two substantially concentric cone portions defining said first and second bonding locations.

18. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

wherein said fitting comprises: a seal housing; and, a seal secured in said housing and comprising a bore being suitable for receiving said medical device and sized to provide an air seal against an outside diameter of said medical device;

further comprising at least one additional bore being suitable for receiving at least one tube for inflating or deflating said dilator.

19. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

wherein said fitting comprises: a seal housing; and, a seal secured in said housing and comprising a bore being suitable for receiving said medical device and sized to provide an air seal against an outside diameter of said medical device;

wherein said seal is mechanically or pneumatically actuatable.

20. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus; and wherein said dilator further comprises at least one of a reflective, partially reflective and absorptive coating.

21. The apparatus of claim 20, wherein said coating comprises at least one of gold, aluminum, silver, titanium oxide and carbon black.

22. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

wherein said fitting comprises: a seal housing; and, a seal secured in said housing and comprising a bore being suitable for receiving said medical device and sized to provide an air seal against an outside diameter of said medical device;

further comprising at least one retainer securing said seal to said housing; and wherein at least two of said housing, seal and retainer are keyed.

23. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

further comprising means for inflating at least said dilator.

24. The apparatus of claim 23, wherein said means for inflating further comprises means for inflating said sheath.

25. A medical device sheath apparatus comprising: a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

wherein said fitting comprises: a seal housing; and, a seal secured in said housing and comprising a bore being suitable for receiving said medical device and sized to provide an air seal against an outside diameter of said medical device; and wherein said seal comprises: a disc portion; an o-ring peripherally positioned with respect to said disk portion; and, a tubular portion extending from said disk portion; wherein said disk portion and tubular portion define at least one bore suitable for receiving said medical device there through.

26. The apparatus of claim 25, further comprising at least one aperture passing through said disk portion, wherein said disk portion is adapted to be compressed between said housing and retainer.

27. A medical device sheath apparatus comprising; a fitting being suitable for receiving said medical device; a seal being suitable for receiving said medical device through said fitting; a sheath for receiving said medical device through said fitting and seal; a dilator defining a treatment area, coupled to said sheath, and being suitable for dilating a bodily cavity and passing energy therethrough; and, a window operatively positioned with respect to said sheath so as to enable viewing of an area substantially adjacent to said sheath upon insertion of said medical device into said apparatus;

wherein said fitting comprises: a seal housing; and, a seal secured in said housing and comprising a bore being suitable for receiving said medical device and sized to provide an air seal against an outside diameter of said medical device;

wherein said housing defines an internal bore corresponding to said bore of said seal, and said housing bore comprises a plurality of internal steps;

wherein said housing further comprises a first bonding location for said first sheath and a second bonding location for said second sheath; and wherein said housing further comprises at least two substantially concentric cone portions defining said first and second bonding locations.

* * * * *